United States Patent
Shimabayashi et al.

(10) Patent No.: US 6,660,855 B2
(45) Date of Patent: Dec. 9, 2003

(54) CRYSTALS OF PENICILLIN AND PROCESS FOR THE PRODUCTION THEREOF

(75) Inventors: Akihiro Shimabayashi, Tokushima (JP); Ichiro Kawahara, Tokushima (JP)

(73) Assignees: Otsuka Chemical Co., Ltd., Osaka (JP); Taiho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/089,075
(22) PCT Filed: Aug. 10, 2001
(86) PCT No.: PCT/JP01/06895
  § 371 (c)(1),
  (2), (4) Date: Apr. 8, 2002
(87) PCT Pub. No.: WO02/14325
  PCT Pub. Date: Feb. 21, 2002

(65) Prior Publication Data
  US 2002/0193588 A1 Dec. 19, 2002

(30) Foreign Application Priority Data
  Aug. 11, 2000 (JP) .......................................... 2000-244288

(51) Int. Cl.$^7$ ............................................. C07D 499/87
(52) U.S. Cl. ...................................................... 540/310
(58) Field of Search .......................................... 540/310

(56) References Cited

U.S. PATENT DOCUMENTS

| | | | |
|---|---|---|---|
| 4,895,941 A | * | 1/1990 | Torii et al. ................... 540/310 |
| 4,912,213 A | * | 3/1990 | Taniguchi et al. ........... 540/310 |
| 6,395,726 B1 | * | 5/2002 | Lin et al. .................... 540/310 |

FOREIGN PATENT DOCUMENTS

| | | |
|---|---|---|
| EP | 0 311 146 A1 | 9/1989 |
| EP | 0 272 016 A1 | 6/1998 |
| JP | 8-53462 | 2/1996 |
| WO | WO 95-12601 A1 | 5/1995 |

* cited by examiner

*Primary Examiner*—Mark L. Berch
(74) *Attorney, Agent, or Firm*—Armstrong, Westerman & Hattori, LLP

(57) ABSTRACT

The crystal of the invention is crystal of diphenylmethyl 2-methyl-2-triazolylmethylpenam-3-carboxylate which is stable substantially without decomposition or degradation of properties even when left to stand at room temperature for 1 year. The crystal of the invention can be prepared by a process comprising the steps of concentrating a solution containing diphenylmethyl 2-methyl-2-triazolylmethylpenam-3-carboxylate represented by the formula (2)

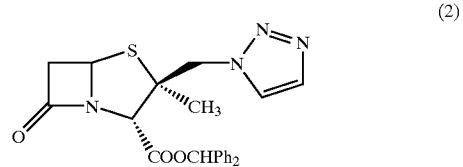

(2)

wherein Ph is a phenyl group, diluting the concentrate with acetic ester and mixing the diluted solution with hexane or a solvent mixture of hexane and acetic ester to crystallize the diphenylmethyl 2-methyl-2-triazolylmethylpenam-3-carboxylate.

1 Claim, No Drawings

CRYSTALS OF PENICILLIN AND PROCESS FOR THE PRODUCTION THEREOF

FIELD OF THE INVENTION

The present invention relates to crystalline penicillin and a process for preparing the same, and more specifically to diphenylmethyl 2-methyl-2-triazolylmethylpenam-3-carboxylate crystal and a process for preparing the same.

BACKGROUND ART

Diphenylmethyl 2-methyl-2-triazolylmethylpenam-3-carboxylate (hereinafter referred to as "TMPB" where appropriate) is a compound useful as an intermediate for preparing tazobactam represented by the formula (1).

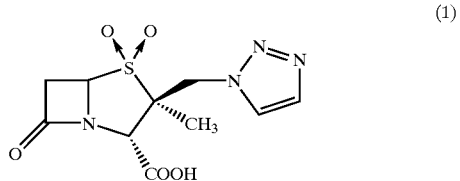

(1)

Tazobactam has a very low antibacterial activity so that it is not used as an antibiotic per se. But it exhibits a beta-lactamase inhibitory activity when irreversibly bonded to beta-lactamases produced by microorganisms. For this reason, tazobactam may be used in mixture with known antibiotics prone to be inactivated by beta-lactamase to allow them to exhibit their inherent antibacterial activity against beta-lactamase-producing microorganisms (Katsuji SAKAI, Recent Antibiotics Manual, $10^{th}$ edition, page 113).

Tazobactam has a chemical structure of having 1,2,3-triazolylmethyl group in the 3-position. Tazobactam is prepared essentially via an intermediate for synthesis of tazobactam such as TMPB, p-nitrobenzyl 2-methyl-2-triazolylmethylpenam-3-carboxylate or the like. Using TMPB, a high-purity tazobactam can be prepared in a high yield by an industrially simple and inexpensive process.

Usually, TMPB is manufactured by the process disclosed, e.g., in Japanese Examined Patent Publication No. 121949/1995. The process comprises the steps of reacting diphenyl-methyl 2-chloromethyl-2-methylpenam-3-carboxylate with 1,2,3-triazole in a solvent in the presence of a base, distilling off the solvent, extracting the mixture with methylene chloride, distilling off the methylene chloride and optionally subjecting the residue to chromatography using silica gel column or the like. Useful solvents include organic solvents such as acetone, acetonitrile and the like, and a solvent mixture of the organic solvent and water.

However, the TMPB-containing solid obtained by the process disclosed in the foregoing publication is unstable since TMPB has a 1,2,3-triazole skeleton having a nucleophilic reactivity in the molecule. For example, when stored at room temperature, the solid decomposes and degrades in properties. It is desirable that an intermediate of pharmaceutical maintains a high purity for a long time and can be stably handled without decomposition or degradation of properties under mild and economical conditions, e.g., for storage at ordinary temperature. For this reason, the TMPB-containing solid obtained by the above-mentioned process is not favorable as an intermediate of pharmaceuticals.

Japanese Unexamined Patent Publication No. 53462/1996, especially in Example 3, discloses that TMPB is produced in a yield of 87% by a process comprising reacting diphenylmethyl 2-methyl-2-aminomethylpenam-3-carboxylate with 2,2-dichloroacetoaldehyde-p-toluenesulfonyl hydrazone in methanol at room temperature, concentrating the reaction mixture, dissolving the residue in methylene chloride, filtering the solution, concentrating the filtrate, and crystallizing the residue in a solvent mixture of ethyl acetate and n-hexane (1:1).

However, the TMPB prepared by such process does not exhibit a clear X-ray powder diffraction pattern, and is in the form of amorphous powder. This TMPB amorphous powder is unstable like the foregoing TMPB-containing solid and is likely to decompose and to degenerate when stored at room temperature (e.g. 5 to 35° C.) for a long time.

DISCLOSURE OF THE INVENTION

An object of the present invention is to provide a TMPB substance which is highly stable and is unlikely to decompose and to change in properties even when stored at room temperature for a long time.

Another object of the invention is to provide a process for preparing a TMPB substance which is highly stable and is unlikely to decompose and to change in properties even when stored at room temperature for a long time.

The present inventors conducted extensive research to achieve these objects, and succeeded in producing TMPB crystals which are different in properties from known TMPB-containing solid and amorphous powder. Based on this novel finding, the invention has been completed.

According to the invention, there is provided a TMPB crystal (hereinafter referred to as "crystalline penicillin") characterized by having peaks at the following interplanar spacings in the X-ray powder diffraction pattern obtained by copper radiation of $\lambda = 1.5418$ angstroms through a monochromator.

d (interplanar spacing)
9.026–9.977
7.192–7.949
6.056–6.694
4.810–5.317
4.662–5.153
4.509–4.984
4.193–4.635
4.120–4.554
4.043–4.447
3.801–4.201
3.602–3.981
3.421–3.781
3.031–3.350

According to the invention, there is provided a process for preparing a crystalline penicillin, the process comprising the steps of concentrating a solution containing TMPB represented by the formula (2)

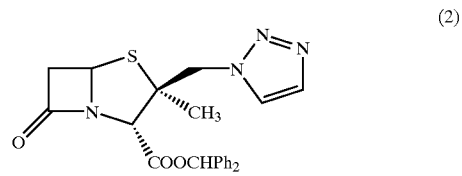

(2)

wherein Ph is a phenyl group, diluting the concentrate with acetic ester, and mixing the diluted solution with hexane or a solvent mixture of hexane and acetic ester to crystallize the TMPB out of the solution.

The crystalline penicillin of the invention, although having a 1,2,3-triazole skeleton with a nucleophilic reactivity in the crystal molecule, is stable without likelihood to decompose and to degenerate even when stored at room temperature for a period of one year or longer, and can retain the high purity, e.g. 90% or higher (especially 95% or higher). With this feature, the crystalline penicillin of the invention is very useful as an intermediate of tazobactam or like pharmaceuticals.

Using the crystalline penicillin of the invention, tazobactam having a purity of 99.9% or higher can be prepared in a yield of 91% or higher.

TMPB of the Invention

The TMPB of the invention is represented by the formula (2)

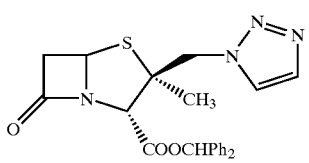

(2)

wherein Ph is as defined above.

The crystalline penicillin of the invention is composed of TMPB crystals having peaks in the above X-ray powder diffraction spectrum. An example includes the crystals having the X-ray powder diffraction spectrum shown below:

| d (interplanar spacing) | Relative intensity(I/Io) |
|---|---|
| 9.026–9.977 | 1.00 |
| 7.192–7.949 | 0.32–0.47 |
| 6.056–6.694 | 0.10–0.16 |
| 4.810–5.317 | 0.46–0.55 |
| 4.662–5.153 | 0.10–0.19 |
| 4.509–4.984 | 0.35–0.65 |
| 4.193–4.635 | 0.20–0.22 |
| 4.120–4.554 | 0.19–0.25 |
| 4.043–4.447 | 0.19–0.31 |
| 3.801–4.201 | 0.13–0.19 |
| 3.602–3.981 | 0.05–0.07 |
| 3.421–3.781 | 0.11–0.17 |
| 1.031–3.350 | 0.06–0.09 |

In the invention, the X-ray powder diffraction spectrum was measured with use of RINT2000/PC manufactured by Rigaku International Corporation.

Process for Preparing TMPB of the Invention

The crystalline penicillin of the invention can be prepared by concentrating a solution containing TMPB, diluting the concentrate with acetic ester, and mixing the diluted solution with hexane or a solvent mixture of hexane and acetic ester.

The TMPB-containing solution can be prepared, for example, by the known process disclosed in Japanese Examined Patent Publication No.121949/1995. For example, the TMPB-containing solution which can be used in the invention may be a reaction solution prepared by reacting diphenylmethyl 2-halomethyl-2-methylpenam-3-carboxylate with 1,2,3-triazole in a solvent or a reaction solution prepared by distilling off the solvent from the above-mentioned reaction solution and dissolving the residue in a suitable solvent such as methylene chloride, acetone, acetonitrile or the like.

The content of TMPB in the TMPB-containing solution is not limited and can be suitably selected from a wide range. Usually it is in the range of about 0.5 to about 15% by weight, preferably about 3 to about 10% by weight.

The amount of 1,2,3-triazole to be used in the reaction between diphenylmethyl 2-halomethyl-2-methylpenam-3-carboxylate and 1,2,3-triazole is in the range of about 1 to about 40 mole equivalents, preferably about 15 to about 35 mole equivalents, per mole of diphenylmethyl 2-halomethyl-2-methylpenam-3-carboxylate. Solvents useful in the reaction are organic solvents such as methylene chloride, acetone, acetonitrile and the like or a solvent mixture of the organic solvent and water. The amount of the solvent to be used in the reaction is not limited and is suitably selected from the range which can easily dissolve the two compounds as the raw materials and which does not hinder the reaction.

A base may be present in the reaction system. Useful bases can be selected from a wide range of known bases such as sodium hydrogencarbonate, potassium hydrogencarbonate and like alkali metal carbonates; barium carbonate, calcium carbonate and like alkaline earth metal carbonates; silver carbonate, copper carbonate and like copper family metal carbonates; copper oxide, silver oxide and like copper family metal oxides; magnesium oxide, calcium oxide, barium oxide and like alkaline earth metal oxides; zinc oxide, mercury oxide and like zinc family metal oxides; aluminum oxide, thallium oxide and like aluminum family metal oxides; silica gel; tin oxide, lead oxide and like carbon family metal oxides; iron oxide, cobalt oxide, nickel oxide and like iron family metal oxides; copper hydroxide, silver hydroxide and copper family metal hydroxides; pyridine, triethylamine, diisopropylethylamine and like organic amines; anion exchange resin and the like. These bases can be used either alone or in combination of two or more species.

The amount of the base to be used is not limited, and is usually about 0.5 equivalent to about 2 equivalents, preferably about 0.6 to about 1.8 equivalents, per equivalent of diphenylmethyl 2-halomethyl-2-methylpenam-3-carboxylate.

The above-mentioned reaction is carried out at a temperature in the range of usually about 0 to about 60° C., preferably room temperature to about 40° C. and is completed in about 0.5 to about 20 hours, preferably about 2 to about 15 hours.

The TMPB-containing solution is concentrated until the amount of the solution is reduced to about ⅕ to about ½ the amount before concentration. The method of concentration is not limited, and known methods can be employed. For example, the concentration is conducted under reduced pressure in the range of about 25 to about 80 kPa.

Thereafter an acetic ester is added to the concentrated TMPB-containing solution (hereinafter referred to merely as "concentrate") to obtain a diluted solution. In this operation, another solvent may be added together with the acetic ester to facilitate the ensuing operations.

Useful acetic esters include those known, such as methyl acetate, ethyl acetate, butyl acetate, and like esters of alcohol having 1 to 4 carbon atoms with acetic acid. Among them, ethyl acetate is preferred. These acetic esters can be used either alone or in combination of two or more. The amount of acetic ester to be used is not limited, and it is usually about 40 to about 240 volumes, preferably about 50 to about 150 volumes, per 100 volumes of the organic solvent remaining in the concentrate.

Other solvents to be added together with acetic ester are not limited and are preferably the same as those remaining in the concentrate. When another solvent is added together with acetic ester, acetic ester is used in the same volume ratio as above, per 100 volumes of total amount of the solvent remaining in the concentrate and another solvent to be added.

The concentration and dilution step of the solution may be repeated to increase the crystallization ratio in the crystallization step and to increase the yield of the contemplated crystalline penicillin of the invention. The concentration may be carried out in the same manner as above. When the dilution is repeated twice or more than two times, acetic ester(s) and optionally other solvent(s) (such as methylene chloride, acetone, acetonitrile or the like) are added to the concentrate. In this operation, acetic ester(s) is added thereto such that about 100 to about 800 volumes, preferably about 200 to about 600 volumes, of acetic ester(s) is present per 100 volumes of other solvent(s) in view of acetic ester(s) and other solvent(s) remaining in the concentrate. The proportions of acetic ester(s) and other solvent(s) than acetic ester(s) in the diluted solution can be determined by analysis using gas chromatography or like analyzer.

The thus-obtained diluted solution is mixed with hexane (s) or a mixture of hexane(s) and acetic ester(s), whereby crystalline penicillin composed of TMPB crystals of the invention is formed. The hexane which can be used in this invention includes known hexanes such as n-hexane, cyclohexane, methylcyclohexane and the like, among which n-hexane is preferred. Useful acetic esters include those exemplified above. The hexanes or acetic esters can be used either alone or in combination.

The amounts of hexane and acetic ester to be used are not limited and can be suitably selected from a wide range. The amount of hexane to be used is about 100 to about 500 volumes, preferably about 150 to about 300 volumes, per 100 volumes of the solvent other than acetic ester in the diluted solution. The amount of acetic ester to be used is about 100 to about 800 volumes, preferably about 200 to about 600 volumes, per 100 volumes of the solvent other than acetic ester in the diluted solution. The proportions of acetic ester and other solvent than acetic ester in the diluted solution can be determined by analysis using gas chromatography or like analyzer.

The temperature condition in crystallization step is not limited and is usually about 20° C. or higher, preferably about 22 to about 40° C. to increase the crystallization ratio and to enhance the yield of the contemplated crystalline penicillin of the invention.

The TMPB crystals thus formed can be easily isolated from the mixture and purified, e.g. by filtration, washing with an organic solvent, drying under reduced pressure or like known isolation means. Organic solvents to be used in washing include, for example, the above-exemplified acetic esters, the above hexanes, solvent mixtures thereof and the like. The mixing ratio of acetic ester and hexane when mixed is not limited. The mixing ratio of hexane relative to acetic ester (ratio by volume) is about 1/10 to about 2. Acetic ester and hexane in substantially the same volume are preferably mixed together. Drying is conducted at about 25 to about 40° C. under reduced pressure in the range of about 30 to about 0.1 kPa.

The crystalline penicillin of the invention can be made into tazobactam useful as a beta-lactamase inhibitor by known methods such as the method illustrated by the reaction scheme given below. Reaction Scheme

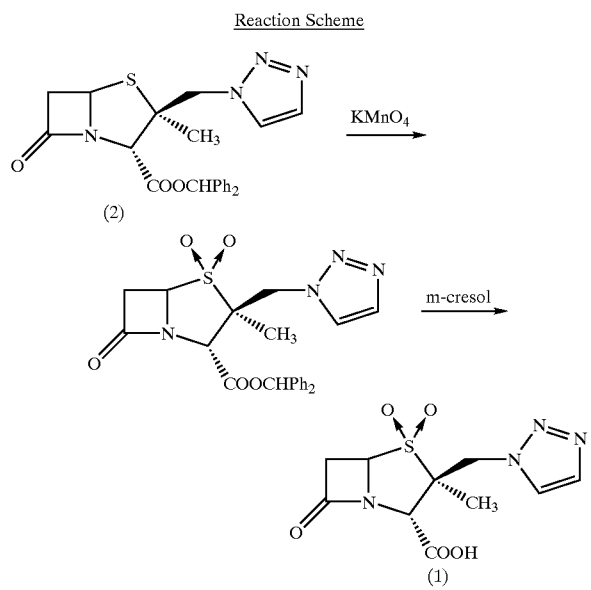

wherein Ph is as defined above.

BEST MODE FOR CARRYING OUT THE INVENTION

The present invention will be described below in more detail with reference to the following examples. However, the scope of the invention is not limited by these examples.

EXAMPLE 1

A 1-liter eggplant-type flask was charged with 300 ml of a methylene chloride solution containing about 15 g of diphenylmethyl 2-methyl-2-triazolylmethylpenam-3-carboxylate. The solution was concentrated under reduced pressure. The methylene chloride distilled off by concentration was recovered as a liquid by passing through a condenser in which a refrigerant (−10 to −20° C.) was refluxed. When the amount of the recovered liquid reached about 210 ml, 43 ml of ethyl acetate was added. The concentration was continued until the amount of recovered organic solvent reached about 60 ml.

The concentrate was analyzed by gas chromatography. Methylene chloride and ethyl acetate were added to the concentrate in amounts such that 10 ml of methylene chloride and 40 ml of ethyl acetate were present in the diluted solution.

Diphenylmethyl 2-methyl-2-triazolylmethylpenam-3-carboxylate precipitated in a crystalline form by adding 24 ml of n-hexane while retaining the solution temperature at 22° C. or higher.

The precipitate was collected by filtration under increased pressure and was washed with 40 ml of an ethyl acetate/n-hexane solvent mixture (volume ratio 50:50). The precipitate was dried under reduced pressure at about 40° C., giving 9.5 g of crystal of diphenylmethyl 2-methyl-2-triazolylmethylpenam-3-carboxylate, which was found to have a purity of 96% as measured by HPLC.

The X-ray powder diffraction pattern obtained by copper radiation of $\lambda=1.5418$ angstroms through a monochromator was measured, and was found to have high peak intensity at the following interplanar spacings.

| d (interplanar spacing) | (Relative intensity) |
| --- | --- |
| 9.5016 | 1.00 |
| 7.5703 | 0.42 |
| 6.3749 | 0.14 |
| 5.0635 | 0.52 |
| 4.9078 | 0.16 |
| 4.7462 | 0.45 |
| 4.4140 | 0.21 |
| 4.3372 | 0.23 |
| 4.2348 | 0.27 |
| 4.0010 | 0.17 |
| 3.7921 | 0.06 |
| 3.6014 | 0.15 |
| 3.1907 | 0.08 |

| d (interplanar spacing) | (Relative intensity) |
| --- | --- |
| 9.5220 | 1.00 |
| 7.5703 | 0.37 |
| 6.3749 | 0.12 |
| 5.0635 | 0.49 |
| 4.9132 | 0.13 |
| 4.7462 | 0.55 |
| 4.4184 | 0.21 |
| 4.3414 | 0.21 |
| 4.2388 | 0.23 |
| 4.0010 | 0.15 |
| 3.7921 | 0.06 |
| 3.6043 | 0.13 |
| 3.1907 | 0.07 |

The $^1$H-NMR spectrum data of the obtained crystal are as follows.

$^1$H-NMR (CDCl$_3$) δ ppm: 1.22 (s, 3H), 3.18 (d, J=16 Hz, 1H), 3.68 (dd, J=4.16 Hz, 1H), 4.59 (m, 2H), 4.86 (s, 1H), 5.42 (d, J=4 Hz, 1H), 6.90 (s, 1H), 7.32 (s, 10H), 7.74 (s, 2H)

Comparative Example 1

A 1-liter eggplant-type flask was charged with 300 ml of a methylene chloride solution containing 15 g of diphenylmethyl 2-methyl-2-triazolylmethylpenam-3-carboxylate. The solution was concentrated under reduced pressure. The concentrate was subjected to silica gel column chromatography for further concentration, giving a solid residue.

It was confirmed by NMR spectrum that the residue was diphenylmethyl 2-methyl-2-triazolylmethylpenam-3-carboxylate. The X-ray powder diffraction pattern of the residue obtained by copper radiation of λ=1.5418 angstroms through a monochromator was measured. However, it did not show a clear X-ray powder diffraction pattern.

Comparative Example 2

A 1-liter eggplant-type flask was charged with 300 ml of a methylene chloride solution containing about 15 g of diphenylmethyl 2-methyl-2-triazolylmethylpenam-3-carboxylate. The solution was concentrated under reduced pressure. The concentrate was subjected to crystallization using a 1:1 solvent mixture of ethyl acetate and n-hexane, whereby a powder of diphenylmethyl 2-methyl-2-triazolylmethylpenam-3-carboxylate was obtained.

The X-ray powder diffraction pattern of the product obtained by copper radiation of λ=1.5418 angstroms through a monochromator was measured. However, the pattern was unclear and the powder was found amorphous.

EXAMPLE 2

The solid residue (18 g) obtained in Comparative Example 1 was dissolved in 280 ml of methylene chloride. The solution was placed into a 1-liter eggplant-type flask. The same subsequent procedure as in Example 1 was carried out, giving 9.5 g of crystal of diphenylmethyl 2-methyl-2-triazolylmethylpenam-3-carboxylate. The crystal had a purity of 96% as determined by HPLC.

The X-ray powder diffraction pattern obtained by copper radiation of λ=1.5418 angstroms through a monochromator was measured and was found to have high peak intensity at the following interplanar spacings.

Reference Example 1

A test tube was charged with 10 g of each of the TMPB crystal of Example 1 (purity 96%), the TMPB crystal of Example 2 (purity 96%), the TMPB-containing solid residue of Comparative Example 1 (purity 83%) and the TMPB amorphous powder of Comparative Example 2 (purity 55%). The test tubes were sealed and stored at room temperature (5 to 35° C.) for 1 year after which their purity was determined by HPLC.

The results are as follows: the purity of TMPB crystal of Example 1 was 96%, the purity of TMPB crystal of Example 2 was 96%, the purity of TMPB-containing solid residue of Comparative Example 1 was 76%, and the purity of TMPB amorphous powder of Comparative Example 2 was 48%.

The crystalline TMPB of the invention had a purity-lowering ratio of 1% or less, namely the purity was substantially not reduced, when stored at room temperature for 1 year.

Reference Example 2

Preparation of White Crystal of Tazobactam

A 1-liter 4-necked flask was charged with 240 ml of methylene chloride and then with diphenylmethyl 2-methyl-2-triazolylmethylpenam-3-carboxylate, which was dissolved in the former. To the solution were added 120 ml of a 90% aqueous solution of acetic acid and 20 g of potassium permanganate. The mixture was stirred at about 42° C. for 3 hours. Added thereto were 340 ml of methylene chloride and 180 ml of water. The mixture was cooled to 5° C. and 24 ml of 35% hydrogen peroxide was added dropwise in a manner to take care of bubbling. The organic layer was separated and washed successively with a 2% aqueous solution of sodium bisulfite and with water. The organic layer was dried and the methylene chloride was distilled off under reduced pressure, whereby 37.4 g of an oily substance was obtained.

Into a 1-liter eggplant-type flask was weighed out 30 g of amorphous powder of diphenylmethyl 2-methyl-2-triazolylmethylpenam-3-carboxylate 1,1-dioxide. The powder was dissolved in 580 ml of methylene chloride. The methylene chloride was concentrated under reduced pressure. When about 420 ml of methylene chloride was distilled off, 400 ml of methanol was added. The concentration was further continued to thereby distill off about 200 ml of the solvent mixture of methylene chloride and methanol. The residue was stirred at 5° C. or lower for 1 hour, whereby diphenylmethyl 2-methyl-2-triazolylmethylpenam-3-carboxylate 1,1-dioxide was precipitated as crystal. The crystal was filtered under reduced pressure, was washed with methanol, and was dried at about 40° C. under reduced pressure, giving 28.5 g of crystal of diphenylmethyl 2-methyl-2-triazolylmethylpenam-3-carboxylate 1,1-dioxide.

Then, 10 g of crystal of diphenylmethyl 2-methyl-2-triazolylmethylpenam-3-carboxylate 1,1-dioxide (TAZB) was added to 80 ml of m-cresol heated to 50 to 55° C. A reaction was performed for 2 hours while maintaining the temperature. After completion of the reaction, 240 ml of methyl isobutyl ketone was added and the mixture was cooled to 0 to 5° C. Added thereto were 23 ml of water and 2.3 g of sodium hydrogencarbonate for extraction. To the organic layer were added 12 ml of water and 0.7 g of sodium hydrogencarbonate for further extraction. The aqueous layers separated by two extraction operations were collected and washed with 18 ml of methyl isobutyl ketone and cooled to 0 to 5° C. A 6N hydrochloric acid was added to adjust the pH to 1. The precipitate was collected by filtration, washed with a small amount of cold water and dried, whereby white crystal of tazobactam was obtained (purity 99.9% and yield 95% based on TAZB).

What is claimed is:

1. A process for preparing the crystalline diphenylmethyl 2-methyl-2-triazolylmethylpenam-3-carboxylate, the process comprising the steps of concentrating a solution containing diphenylmethyl 2-methyl-2-triazolylmethylpenam-3-carboxylate represented by the formula (2):

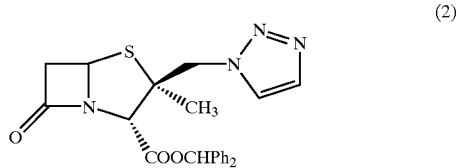

(2)

wherein Ph is a phenyl group, diluting the concentrate with an acetic ester, and mixing the diluted solution with hexane or a solvent mixture of hexane and an acetic ester to crystallize the diphenylmethyl 2-methyl-2-triazolylmethylpenam-3-carboxylate.

* * * * *